US006324414B1

(12) United States Patent
Gibbons et al.

(10) Patent No.: US 6,324,414 B1
(45) Date of Patent: Nov. 27, 2001

(54) TUNNELING LEAD TERMINAL HAVING A DISPOSAL SHEATH

(75) Inventors: Paul Gibbons, Ilkley (GB); Timothy Beardsley, Kingston; Terrence Young, Taunton, both of MA (US)

(73) Assignee: Depuy Orthopaedics, Inc., Warsaw, IN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/313,827

(22) Filed: May 18, 1999

(51) Int. Cl.$^7$ .......................................... A61B 5/00
(52) U.S. Cl. .......................... 600/373; 600/378; 606/129
(58) Field of Search ................................... 600/372, 373, 600/379, 377, 378, 380, 381, 544; 606/129, 130; 607/36, 37, 119, 122; 439/909

(56) References Cited

U.S. PATENT DOCUMENTS

| 5,542,173 | * | 8/1996 | Mar et al. ............................ 607/122 |
| 5,782,841 | * | 7/1998 | Ritz et al. ............................. 606/129 |
| 5,871,528 | * | 2/1999 | Camps et al. ......................... 607/199 |

* cited by examiner

Primary Examiner—Linda C. M. Dvorak
Assistant Examiner—David M. Ruddy
(74) Attorney, Agent, or Firm—Nutter, McClennen & Fish, LLP

(57) ABSTRACT

A monitoring system includes a lead having a terminal covered by a removable sheath. In one embodiment, the lead has a first end coupled to an implantable electrode and a second end which includes a terminal for coupling to a mating terminal. The sheath prevents bodily fluids from contacting the terminal as the lead is tunneled under a patient's scalp. After the terminal exits the scalp, the sheath is removed from the terminal to allow its connection to the mating terminal.

20 Claims, 5 Drawing Sheets

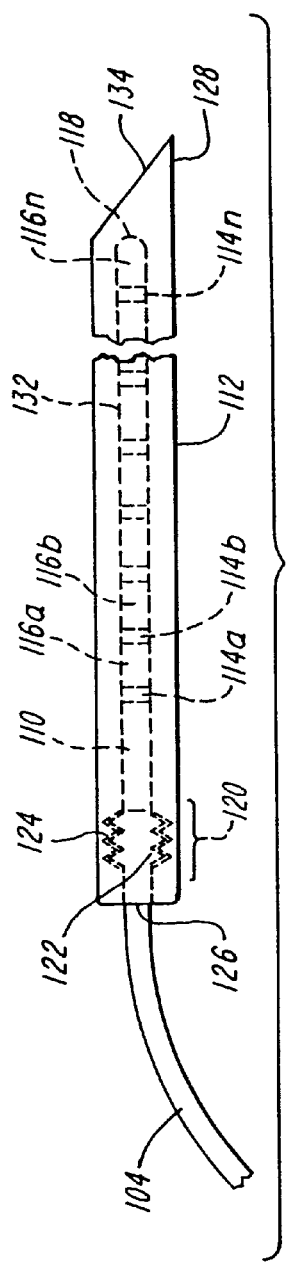
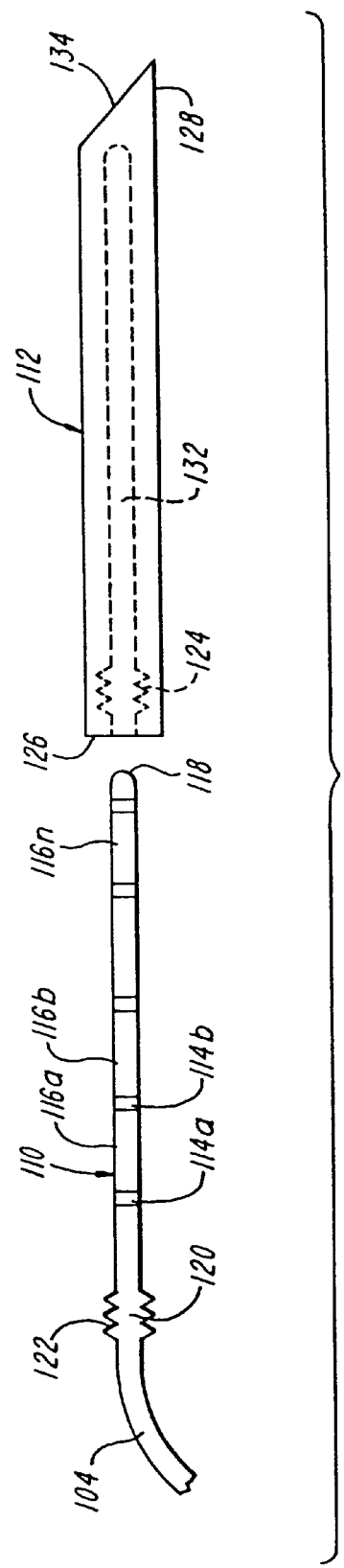

TUNNELING LEAD TERMINAL HAVING A DISPOSAL SHEATH

CROSS REFERENCE TO RELATED APPLICATION

Not Applicable.

STATEMENT REGARDING FEDERALLY SPONSORED RESEARCH

Not Applicable.

FIELD OF THE INVENTION

The invention relates generally to implantable medical devices, and more particularly, to systems having an implantable device coupled to an electrical lead for being tunneled through tissue to allow a connection to a mating terminal.

BACKGROUND OF THE INVENTION

Implantable medical devices are used in a variety of applications. One such medical application includes the monitoring of electrical impulses on the surface of a patient's brain. Tracking electrical activity of the brain is useful in conjunction with the treatment and/or diagnosis of certain medical conditions, such as epilepsy. Exemplary electrodes for contacting the brain are disclosed in U.S. Pat. Nos. 4,903,702 and 5,044,368, which are incorporated herein by reference.

In one technique, electrodes are implanted within the cranium in contact with the patient's brain. To position the electrodes, the surgeon typically forms a hole in the patient's skull for accessing selected tissue. One or more electrodes are positioned on the patient's brain for monitoring its electrical activity. After the electrodes are placed at the desired location, they must be coupled to a remote monitoring device which analyzes the data from the probes. A lead extends from the electrode to provide a signal pathway to the remote monitoring device.

In some procedures used to connect a terminal end of the probe lead to an external mating terminal, a trocar is tunneled under the patient's scalp for a predetermined distance after which it exits the scalp. The terminal end of the electrode lead is then threaded through a passageway in the trocar so that the terminal can be connected to a corresponding mating terminal of a lead coupled to the remote monitoring device.

During this procedure, the exposed terminal of the electrode lead becomes covered with bodily tissue and fluid as it passes through the trocar. Exposure to bodily substances can impair the integrity of an electrical connection between the terminal end of the eleectrode lead and the mating terminal of the remote device lead, which provides a signal path to the remote monitoring device. Due to the relatively high level of sensitivity that is required for accurate detection of signals generated by the brain, any attenuation or interference with the signals from the electrode can render the resulting data useless and/or misleading.

It would, therefore, be desirable to provide a system that is able to preserve the sensitivity of the electrode contacts during implantation within the body.

SUMMARY OF THE INVENTION

The present invention provides a system including a fluid impermeable sheath disposed on a lead terminal for preventing bodily fluids from contacting the terminal. Although the system is primarily shown and described in conjunction with a lead extending from an electrode for intracranial implantation, it is understood that the invention has other applications as well. For example, the electrode can be implanted at other locations in the body, such as in or near, the heart, the intestines and the extremities.

In one embodiment, the system includes an electrode adapted for implantation in the patient's body, such as on the surface of a patient's brain. A lead has a first end coupled to the electrode and a second end that provides an electrical terminal. A fluid impermeable sheath is disposed on the terminal for preventing bodily fluids and tissues from contacting the terminal. The sheath forms a barrier for maintaining the terminal in pristine condition while the lead terminal is tunneled under the patient's scalp and until it ultimately exits the scalp when it can be electrically connected with a mating terminal. The mating terminal can provide a signal path to a remote device for monitoring signals from the electrode and/or electrical stimulation of tissue.

In an exemplary embodiment, the sheath is removably engaged with the lead so as to cover the terminal. The sheath is at least semi-rigid with a distal end having an edge to facilitate tunneling of the lead under the scalp.

In another embodiment, the sheath is a flexible and can be torn away from the terminal after the lead has been tunneled through tissue. In one embodiment, the sheath is formed from a polymeric material which can be shrink-fitted onto the terminal.

BRIEF DESCRIPTION OF THE DRAWINGS

The invention will be more fully understood from the following detailed description taken in conjunction with the accompanying drawings, in which:

FIG. 4 is a side view showing further details of the sheath-covered lead of FIG. 1;

FIG. 5 is a side view showing the lead and sheath of FIG. 5 separated from each other;

DETAILED DESCRIPTION OF THE INVENTION

Figure 1:
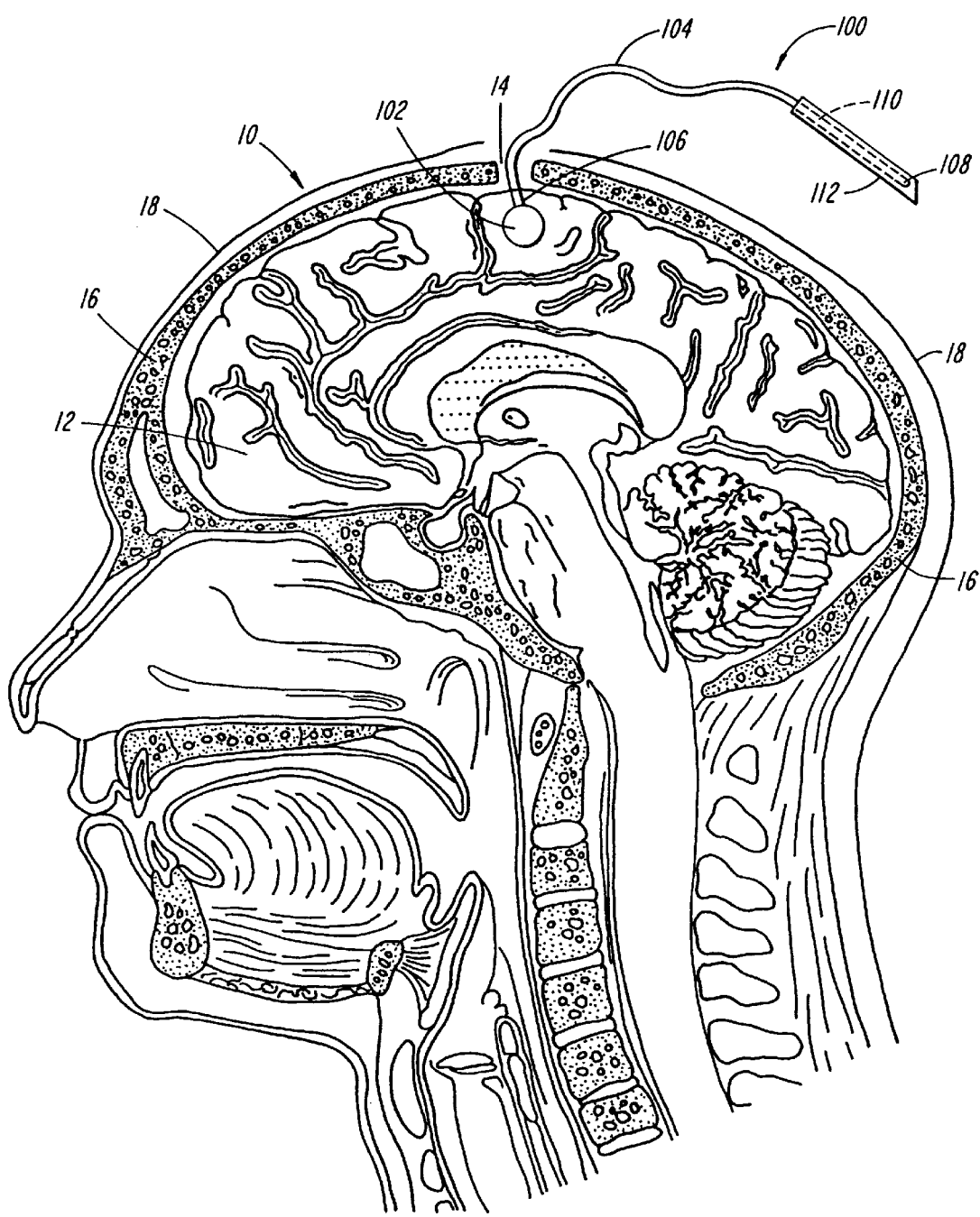
FIG. 1 is a diagrammatic illustration of a system including an implanted probe coupled to a lead having a terminal covered by a protective sheath in accordance with the present invention.
Figure 2:
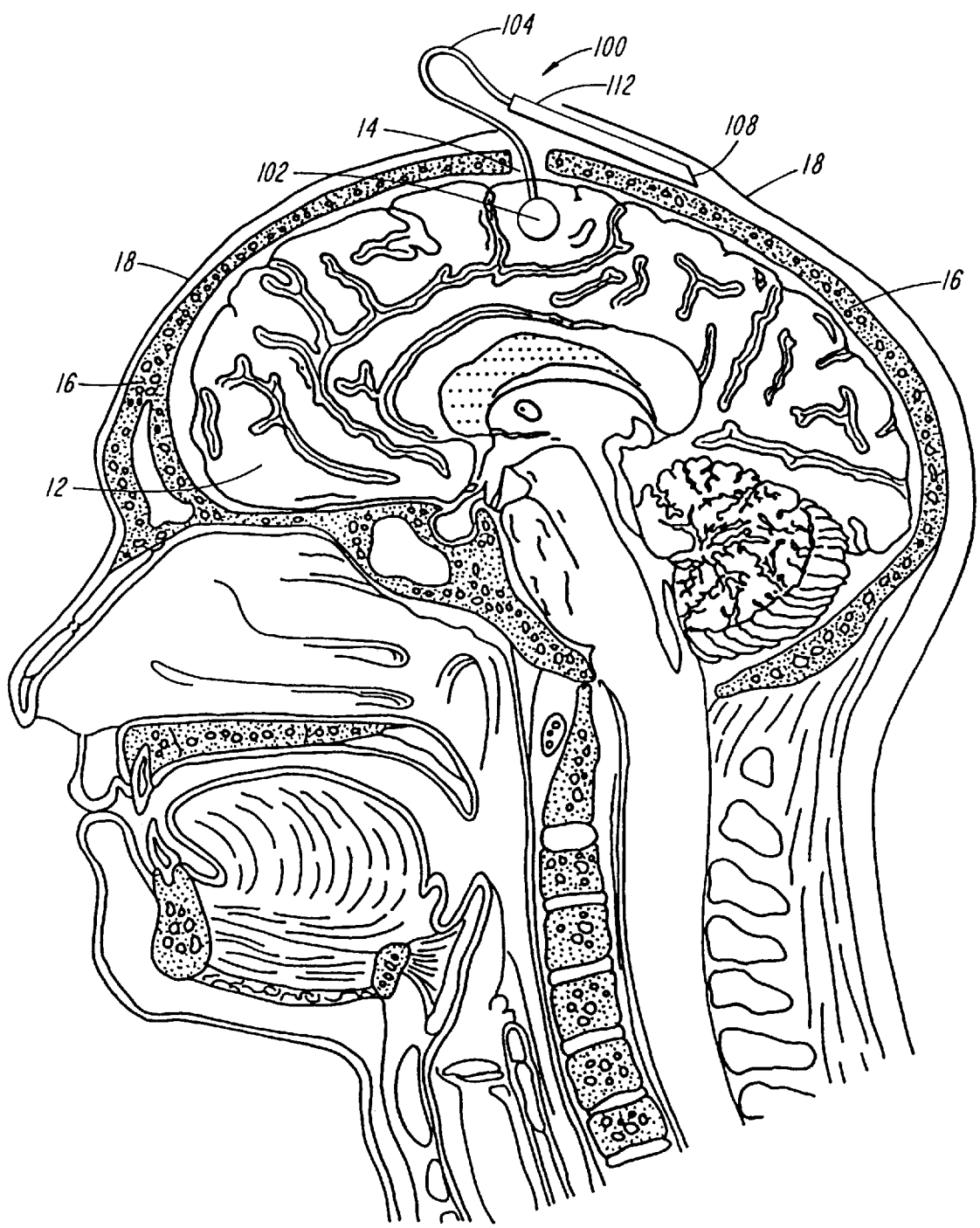
FIG. 2 is a diagrammatic illustration of the system of FIG. 1 shown with the lead being tunneled under a patient's scalp.
Figure 3:
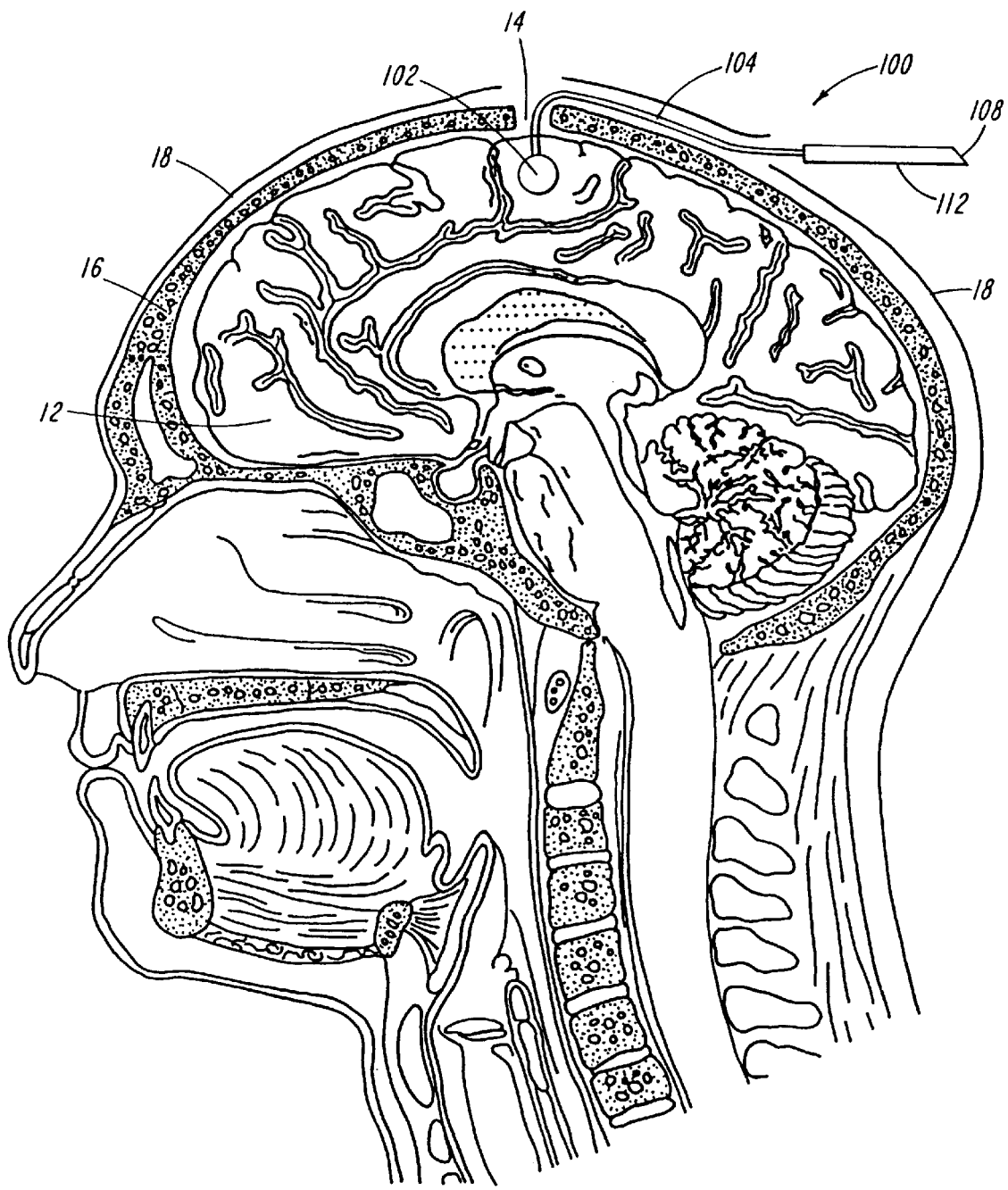
FIG. 3 is a diagrammatic illustration of the system of FIG. 1 shown with the lead exiting the patient's scalp.

FIGS. 1–3 show a system 100 in accordance with the present invention that is partially implantable within a patient's cranium 10. No reference numeral 10 is shown. The system 100 includes an implantable electrode 102 adapted for placement on a surface of the patient's brain 12.

The electrode 102 detects electrical signals from the brain 12 and conveys these signals to a remote monitoring device (not shown). It is understood that the electrode can also deliver electrical signals to the brain. The electrode 102 is placed in contact with the brain 12 via an aperture 14 formed in the patient's skull 16 and scalp 18. A lead 104 has a first end 106 coupled to the electrode 102 and a second end 108 which provides an electrical terminal 110. The terminal 110 is covered by a fluid impermeable sheath 112 for preventing bodily tissue from contacting the terminal 110.

After initially implanting the electrode 102, a surgeon tunnels the lead terminal 110 under the patient's scalp 18 (FIG. 2). While tunneling the lead terminal 110 under the scalp, the sheath 112 forms a barrier between bodily substances and the lead terminal 110. After tunneling under the scalp 18 for a desired distance, the lead terminal 110 exits the scalp (FIG. 3) to allow the terminal to be connected to a corresponding mating terminal (not shown).

The sheath 112 obviates the need for a trocar when tunneling a lead terminal under the scalp. More particularly, in a conventional technique a trocar is tunneled under the patient's scalp after which the uncovered lead terminal is threaded through a passageway in the trocar. In contrast to the sheath 112, a trocar provides little, if any, protection against exposure of a lead terminal to bodily fluids and the like.

The lead terminal 110 can have various structures and geometries depending upon, for example, the intended application. The lead terminal 110 can be elongate, round, cylindrical, triangular, and polygonal. In an exemplary embodiment, the lead terminal is cylindrical.

FIGS. 4–5 show further details of the terminal/sheath assembly 110,112. The lead terminal 110 has a series of contacts in the form of rings 114a–n spaced by insulative sections 116a–n. Each of the rings 114 is connected to a corresponding electrical contact disposed on the implantable electrode 102 (FIG. 1) via a respective conductor (not shown) within the lead 104. The rings 114 provide corresponding signal paths to a female mating conductor for enabling propagation of the signals to (and from) a remote device (not shown).

The terminal 110 has a distal end 118 and a proximal end or base portion 120. The base portion 120 can have a variety of engagement mechanisms for coupling the lead 104 to the sheath 112. Exemplary engagement mechanisms include threads, surface features, interference fits, and adhesive bonds.

In an exemplary embodiment, the base portion 120 has threads 122 disposed thereon for engaging complementary threads 124 disposed on a proximal end 126 of the sheath. It is understood that threaded engagement of the sheath 112 to the terminal 110 forms a substantially fluid impermeable seal against bodily fluids and the like.

The sheath 112 has a structure for receiving and covering the lead terminal 110 such that the terminal contacts 114 remain uncontaminated by any bodily substance. Maintaining the terminal 110, and therefore the ring contacts 114, in a pristine state optimizes the conditions for achieving a reliable electrical connection between the contacts and corresponding electrical contacts on the mating connector (not shown). It is understood that the integrity of the signal from the implanted electrode 102 to a remote monitoring device must be maintained for meaningful analysis of the electrical activity of the brain. And while it may be possible to clean a soiled terminal, some residual tissue and/or cleaning solution can increase the likelihood of a defective or intermittent electrical connection.

The sheath 112 can have a variety of characteristics and structural features based upon the geometry of the lead terminal 110 and the requirements of a particular application. The sheath 112 can vary from extremely rigid to extremely flexible. The geometry of the sheath can be cylindrical, polygonal, smooth, contoured, and surface featured. In general, the sheath 112 is adapted to surround and cover the lead terminal 110.

In an exemplary embodiment, the sheath 112 is rigid and generally cylindrical with a distal end 128 and a proximal end 126. A bore 132 extends from the proximal end 126 of the sheath to a point near the distal end 128. The bore 132 is sized to capture the terminal 110 as the sheath 112 is coupled to the lead 104. Threads 124 on the proximal end 126 of the bore 132 engage the threads 122 on the base 120 of the terminal 110.

In one embodiment, the distal end 128 of the rigid sheath 112 has an edge 134 to facilitate tunneling of the terminal 110 under the patient's scalp. In the exemplary embodiment shown, the edge 134 tapers. Alternatively, the distal end 128 of the sheath converges to a point.

Figure 6:
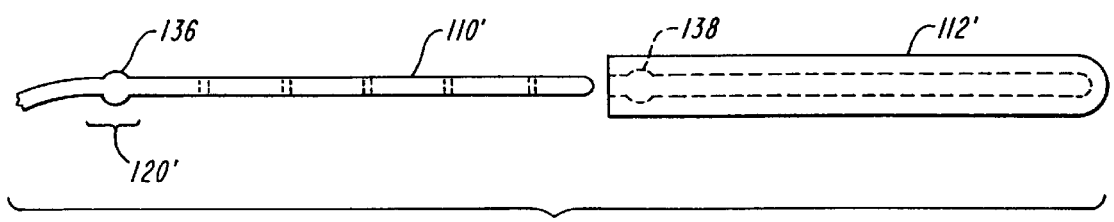
FIG. 6 is a side view of a further embodiment of a lead covered by a sheath in accordance with the present invention.

FIG. 6 shows an alternative embodiment of the sheath/terminal engagement mechanism. The base portion 120' of the terminal 110' includes a raised surface feature 136. The sheath 112' has a corresponding depression 138 to provide a longitudinal snap-fit engagement.

Figure 7:
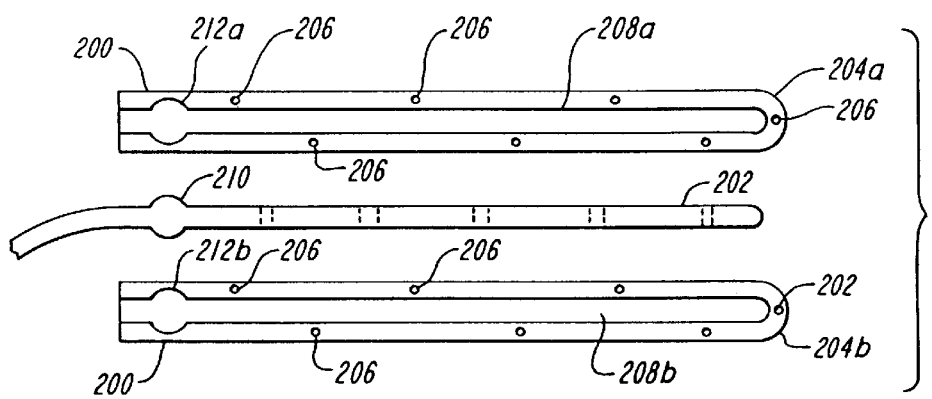
FIG. 7 is a side of another embodiment of a sheath having first and second engagable portions for covering a lead terminal in accordance with the present invention.

FIG. 7 shows a further embodiment of a sheath 200 for protecting a terminal 202 from bodily substances. The sheath 200 has first and second portions 204a,b that snap together to surround the terminal 202. In one embodiment, each of the sheath portions 204a,b has complementary surface features 206, e.g., protrusions and apertures, for retaining the portions together. Channels 208a,b formed in the sheath portions 204a,b are sized to receive the elongate lead terminal. A bump 210 on the base of the terminal 202 and corresponding depressions 212a,b within the channels 208a,b are effective to align the terminal 202 within the sheath portions 204a,b. After use, the sheath portions 204 can be separated and disposed of.

It is understood that the rigidity of the sheath can be varied. Exemplary materials for a rigid sheath include polyethylene, polycarbonate, polypropylene, polyurethane, Nylon, Kynar, polyvinyl chloride, and acrylonitrile-butadiene-styrene copolymer (ABS). It is further understood that an edge or point can be formed from a separate component joined to the body of the sheath. The edge or point can be formed from steels or other such materials for cutting and/or tunneling which are known to one of ordinary skill in the art.

The overall dimensions of the sheath can vary to optimize the device for a particular application. In an exemplary embodiment, the length of the sheath can vary from about one centimeter to about ten centimeters and the diameter of the sheath can vary from about two millimeters to about ten millimeters.

Figure 8:
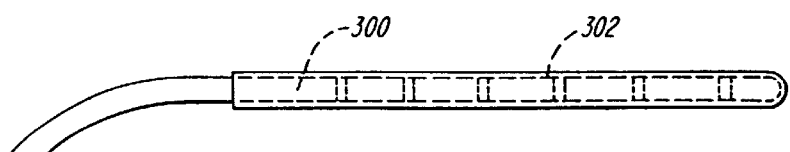
FIG. 8 is a side view of still another embodiment of a lead covered by a sheath in accordance with the present invention.

FIG. 8 shows a lead terminal 300 covered by a flexible, fluid-impermeable sheath 302. The sheath 302 can be formed from a material that can be shrunken to fit snugly over the lead terminal 300. In one embodiment, the terminal 300 is inserted into a relatively loose-fitting sheath 302 and subjected to heat which shrinks the sheath such that it conforms to the outer surface of the terminal 300.

In an alternative embodiment (not shown), the sheath is initially rolled up. The sheath is positioned at the distal end of the terminal and unrolled such that the lead terminal is covered by the sheath.

After use, e.g., after the lead is tunneled under the patient's scalp, the sheath is easily removed from the terminal by tearing it or otherwise disposing of the sheath. Thus, the sheath is disposable while the lead may be re-used.

The thickness of the sheath 202 can vary to achieve a suitable fluid-impermeable barrier for the terminal. An exemplary thickness for the sheath ranges from about 0.1 millimeters to about 2.0 millimeters.

The flexible sheath 202 can be formed from a variety of materials having suitable properties. Exemplary materials include silicone, latex, polyvinyl chloride, Kraton, rubber, and low density polyethylene (LDPE).

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A bio-implantable system for providing an electrical signal path, including:

an implantable electrode;

a lead including a first end coupled to the electrode and a second end, the second end including a lead terminal; and a fluid impermeable sheath disposed over a substantial portion of and removably connectable to the lead terminal, the sheath being effective to prevent bodily fluids from contaminating the lead terminal as the lead terminal is tunneled through tissue.

2. The system according to claim 1, wherein the sheath is rigid.

3. The system according to claim 2, wherein the sheath has a sharpened end for penetrating tissue.

4. The system according to claim 1, wherein the sheath includes first and second engagable components.

5. The system according to claim 1, wherein the sheath is flexible.

6. The system according to claim 5, wherein the sheath is formed from a shrink fit material.

7. The system according to claim 1, wherein the sheath is generally cylindrical.

8. The system according to claim 7, wherein the sheath has a proximal end with a bore for capturing the terminal and a distal end for tunneling through tissue.

9. The system according to claim 1, wherein the sheath is threadably coupled to the lead.

10. The system according to claim 1, wherein the sheath is snap fit to the lead.

11. The system according to claim 1, wherein the electrode includes at least one contact.

12. The system according to claim 11, wherein the terminal is adapted for coupling to a female mating terminal for propagating signals between the electrode and a remote device.

13. A system having at least one implantable component for monitoring a physiological signal and/or stimulating tissue, comprising:

a device for implantation in a patient's body;

an electrical lead having a first terminal coupled to the device and an elongate, cylindrical second terminal, the second terminal for mating with a corresponding female terminal to propagate signals between the device and remote unit; and a disposable sheath disposed over a substantial portion of and connectable to the second terminal, the sheath being effective to prevent bodily fluids from contacting the second terminal as the lead is tunneled through the tissue.

14. The system according to claim 13, wherein the sheath has a proximal end with a bore for receiving the second terminal and a distal end with an edge to facilitate tunneling under a patient's scalp.

15. The system according to claim 13, wherein the sheath has a pointed distal end to facilitate tunneling under a patient's scalp.

16. The system according to claim 13, wherein the sheath is threadably engaged to the lead.

17. The system according to claim 13, wherein the sheath includes at least one surface feature for engaging a corresponding surface feature on the lead.

18. The system according to claim 13, wherein the sheath includes first and second portions for mating with each other so as to cover the second terminal.

19. The system according to claim 13, wherein the sheath is flexible and is formed from a shrink fit material.

20. The system according to claim 13, wherein the sheath is flexible and is adapted for being unrolled onto the second terminal so as to cover it.

* * * * *